United States Patent [19]

Paukkunen

[11] Patent Number: 5,511,417
[45] Date of Patent: Apr. 30, 1996

[54] METHOD AND ARRANGEMENT IN MEASUREMENT OF HUMIDITY, IN PARTICULAR IN RADIOSONDES

[75] Inventor: Ari Paukkunen, Vantaa, Finland

[73] Assignee: Vaisala Oy, Vantaa, Finland

[21] Appl. No.: 313,017

[22] Filed: Sep. 27, 1994

[30] Foreign Application Priority Data

Sep. 29, 1993 [FI] Finland .................................. 934267

[51] Int. Cl.$^6$ .......................... G05D 22/02; G01N 27/02; G01W 1/08
[52] U.S. Cl. .................. 73/335.03; 73/29.01; 73/335.05
[58] Field of Search ........................... 73/335.03, 335.04, 73/335.05, 29.01, 29.02

[56] References Cited

U.S. PATENT DOCUMENTS

| | | | |
|---|---|---|---|
| 3,168,829 | 9/1965 | Nelson | 73/336.5 |
| 3,350,941 | 5/1965 | Misevich et al. | 73/336.5 |
| 3,599,862 | 8/1971 | Hogan | 236/44 C |
| 4,035,644 | 7/1977 | Ciemochowski | 250/340 |
| 4,915,816 | 4/1990 | Shakkottai et al. | 204/430 |
| 5,156,045 | 10/1992 | Ponkala | 73/170 R |
| 5,156,046 | 10/1992 | Ponkala | 73/170 R |
| 5,365,784 | 11/1994 | Morrissey | 73/335.02 |

FOREIGN PATENT DOCUMENTS

| | | |
|---|---|---|
| 0260662 | 3/1988 | European Pat. Off. . |
| 48229 | 4/1974 | Finland . |
| 58403 | 9/1980 | Finland . |
| 58402 | 9/1980 | Finland . |
| 85770 | 2/1992 | Finland . |
| 8165048 | 9/1983 | Japan .................. 73/335.03 |
| 5172776 | 7/1993 | Japan .................. 73/335.03 |
| 2047431 | 11/1980 | United Kingdom . |

*Primary Examiner*—Hezron E. Williams
*Assistant Examiner*—J. David Wiggins
*Attorney, Agent, or Firm*—Jones & Askew

[57] ABSTRACT

Method and detector arrangement for measurement of relative humidity in particular in radiosondes (100). In the humidity detector (14), an active material is used whose electric properties are a function of the amount of water absorbed by said material. The humidity detector (14) is heated so as to remove any ice, frost or condensed humidity gathered on its face and/or in its vicinity. The temperature (T) of the humidity detector (14) and/or the ambient temperature ($T_a$) is/are detected, and this/these quantity/quantities is/are utilized in the computing of the humidity measurement values (U). The humidity detector (14) is protected by means of a mechanical shield construction (10) arranged around the detector. The shield construction (10) is heated to a temperature higher than the ambient temperature so that no substantial condensing or freezing of humidity takes place on the humidity detector (14) or on the structures in the vicinity of same.

11 Claims, 4 Drawing Sheets

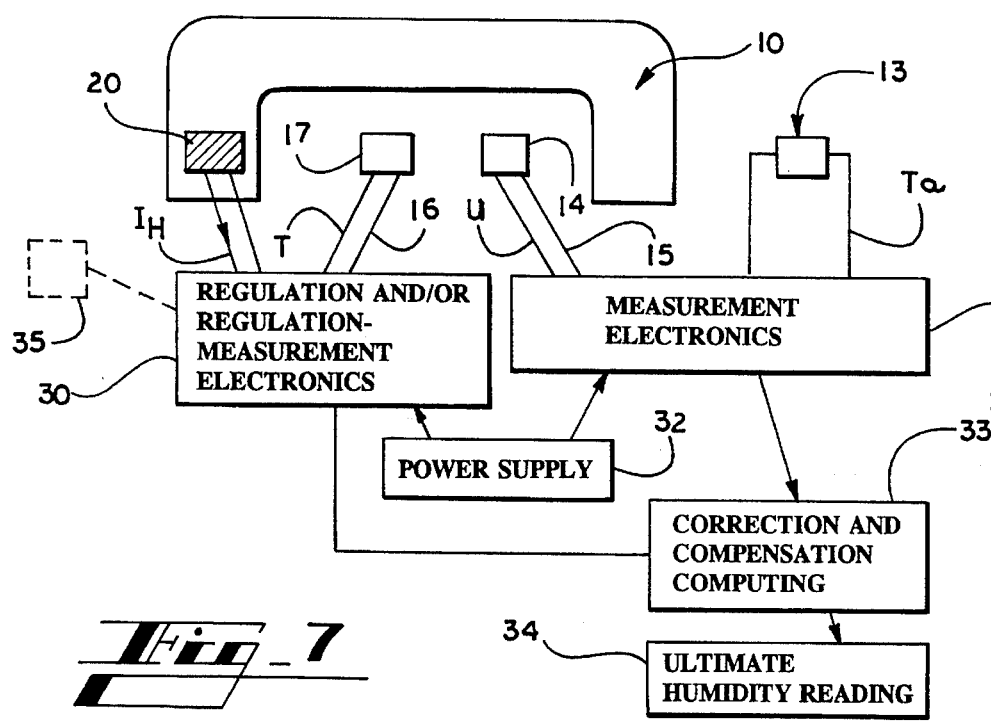
Fig_7
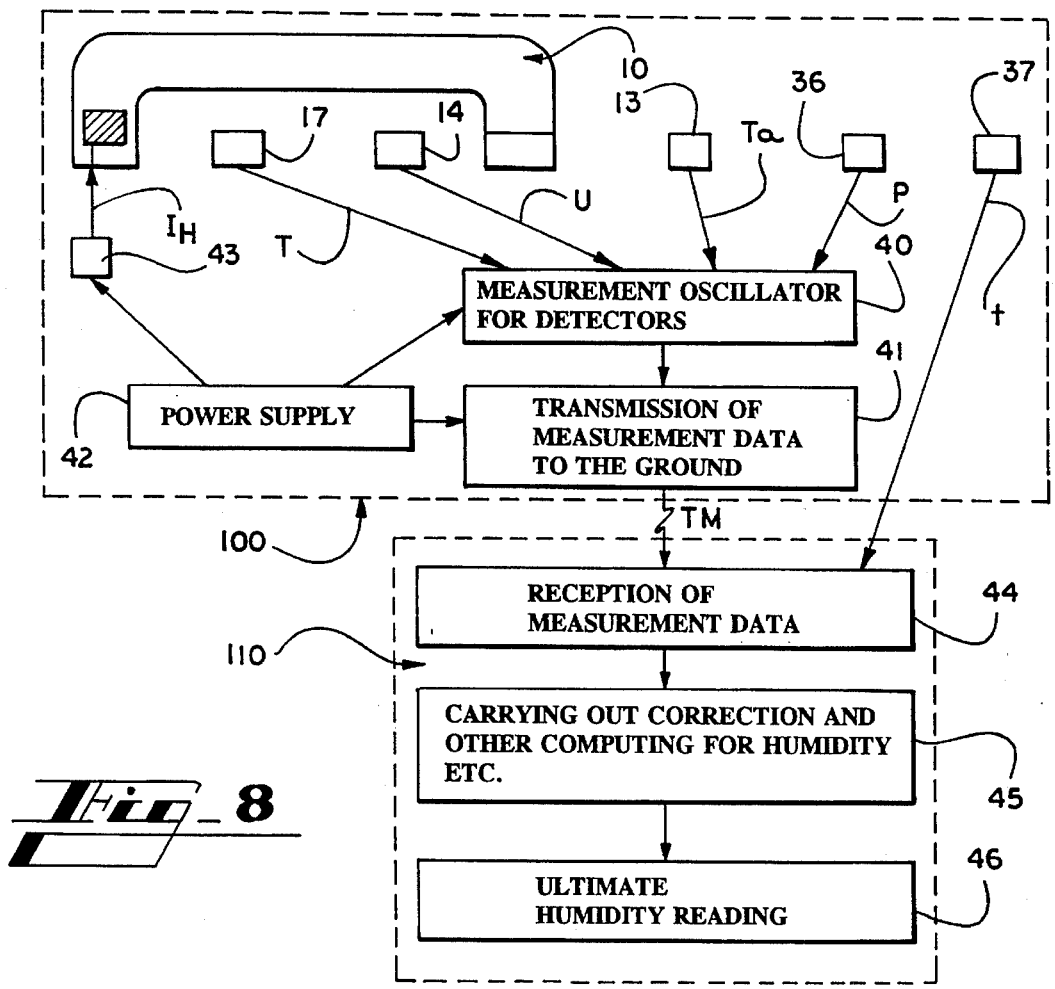
Fig_8

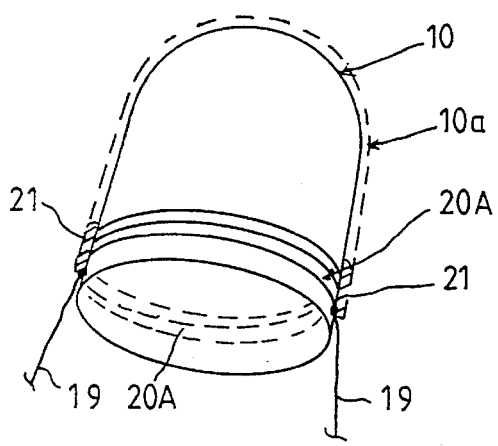
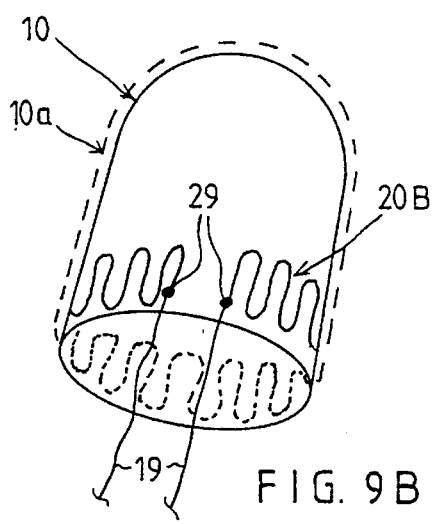
FIG. 9A    FIG. 9B
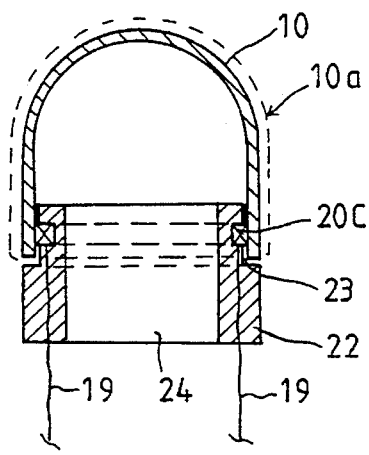
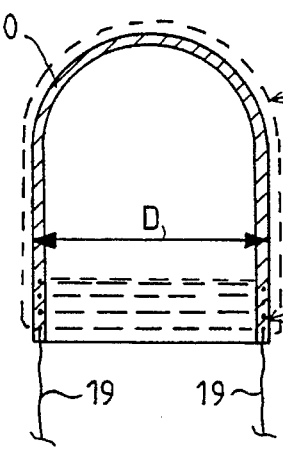
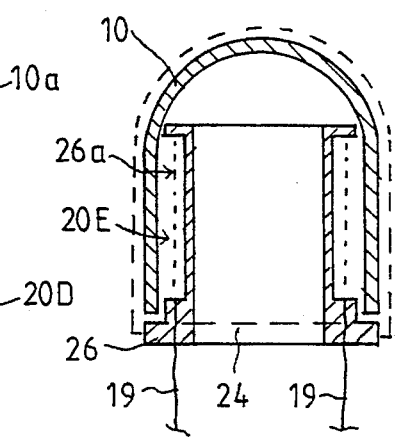
FIG. 9C    FIG. 9D    FIG. 9E
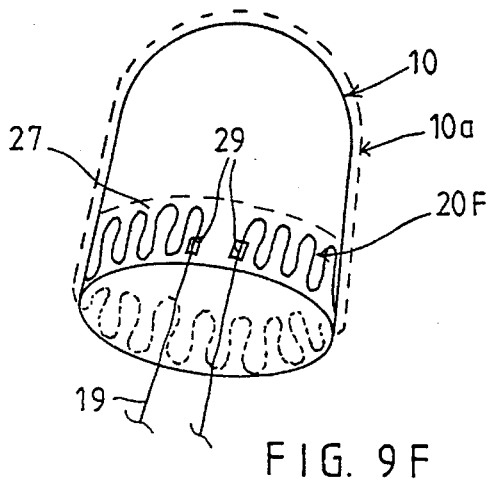
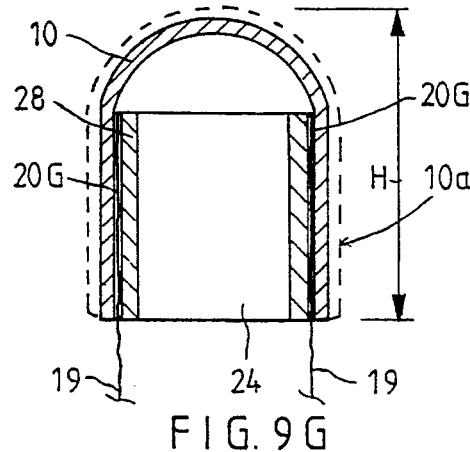
FIG. 9F    FIG. 9G

METHOD AND ARRANGEMENT IN MEASUREMENT OF HUMIDITY, IN PARTICULAR IN RADIOSONDES

The invention concerns a method for measurement of relative humidity by using a humidity detector, in particular in radiosondes, in which humidity detector an active material is used whose electric properties are a function of the amount of water absorbed by said material, in which method said detector is heated so as to remove any ice, frost or condensed humidity gathered on its face and/or in its vicinity, in which method the temperature of the humidity detector and/or the ambient temperature is/are detected and this/these quantity/quantities is/are utilized in the computing of the humidity measurement values, and in which method the humidity detector is protected by means of a mechanical shield construction arranged around the detector.

Further, the invention concerns a detector arrangement, in particular for radiosondes, for measurement of the relative humidity of the environment, which detector arrangement comprises a humidity measurement detector and a detector for measurement of its temperature as well as a shield that surrounds said detectors, which detector arrangement includes a heating resistor, to which electric current is fed, by whose means the humidity detector and its environment are heated, and which arrangement further includes a detector for measurement of the ambient temperature.

In the prior art, a number of different electrically detected temperature and humidity detectors are known whose impedance changes as a function of the quantity to be measured. Such humidity detectors are known, e.g., from the U.S. Pat. Nos. 3,168,829 and 3,350,941 and from the applicant's Finnish Patent No. 48,229.

The FI Patent No. 48,229 is related to the prior art concerned in the present invention, in which patent a capacitive humidity detector is described in which the dielectric insulating material is a polymer film whose permittivity is a function of the amount of water absorbed by the polymer film.

As is known in the prior art, also for measurement of temperature, capacitive detectors are used, which are usually based on the fact that the permittivity of the insulating material between the capacitor plates is dependent on the temperature, in which case the capacitance detected from the terminals of the detector also depends on the temperature.

In the detectors described above and also in other detectors based on change in impedance, undesirable phenomena occur, which;include freezing and wetting of detectors, radiation error, slowness of the detectors, and hysteresis.

In the applicant's FI Patent No. 58,402, a method is described for reduction of undesirable properties produced by reversible changes in an electric humidity detector based on change in impedance, in particular in a capacitive humidity detector, in which the material sensitive to humidity is an organic polymer, which is heated, at least with higher relative humidities, to a temperature higher than the temperature in the environment of the humidity detector. If necessary, the heating power of the detector can be regulated as a function of the humidity to be measured. In said FI patent, the temperature of the humidity detector and/or the ambient temperature is/are measured, and this or these auxiliary quantities are utilized in the computing of the humidity measurement values.

Regarding the prior art, reference is made further to the applicant's FI Patent No. 58,403 (corresponding GB Patent No. 2,047,431), wherein a regulating device in a humidity detector is described, which comprises a bridge connection or equivalent, which includes temperature-dependent resistor elements, by whose means the temperature outside the detector and the temperature $T_s$ of the detector itself are detected, the differential voltage in said bridge connection being used as a feedback signal, by whose means the electric power that heats the detector is regulated.

With respect to the prior art related to the present invention, reference is made further to the applicant's FI Patent No. 85,770 (corresponding U.S. Pat. No. 5,156,045), wherein a method is described in connection with impedance detectors for radiosondes, in which method the temperature of the detector or detectors is measured by means of a thermocouple, in which the connection of one branch of its thermoelements is placed in connection with, or at the proximity of, the detector to be measured, and in which thermocouple the connection of the other branch is placed in the atmosphere surrounding the detector, and in which method, by means of said thermocouple, the difference between the temperature prevailing in connection with the detector and the temperature of the surrounding atmosphere is observed, an electric signal that represents said difference acting upon the output signal of the measurement coupling of the radiosonde, which signal includes the information on the meteorological quantity or quantities to be measured by means of the detector or detectors.

The general object of the present invention is further development of the prior-art technique of measurement of relative humidity, in particular in radiosonde applications, so that the drawbacks, to be described in more detail later, are avoided.

It is an object of the invention to provide novel methods of measurement and novel detectors, in particular for radiosonde operation, in which the capacitive humidity detector is subjected to such a high humidity that the detector operation deteriorates and water, frost, and/or ice is/are gathered and condensed on the active face of the detector or on the structures in its environment. When such a situation of disturbance is over, it takes a long time before the water or ice has evaporated, during which period of time the detector, of course, gives an erroneous message, indicating an excessively high humidity. Some of the drawbacks mentioned above can be avoided by means of the heating of the capacitive humidity detector described in the above FI Patent 58,402, but it still remains a problem with no satisfactory solution that, in order that a sufficiently accurate measurement of humidity could be provided, the temperature of the humidity detector must also be known highly accurately. In order that an accuracy of ~1 ... 2% of measurement of relative humidity could be achieved, it must be possible to measure the temperature of the detector at a precision of ~0.1° C. In the measurement of the temperature, there may be a higher absolute error, but the difference in temperature as compared with the environment must be known at said precision. Thus, the principal object of the invention is to provide a humidity detector by whose means it is possible to avoid the drawbacks produced by condensing and freezing of water on the face of the humidity detector and/or on the structures in its environment, for example, when a radiosonde flies in a supercooled cloud.

The object of the invention is to provide a method of measurement and detectors by whose means relative humidity can be measured at least at the precision of ~1 ... 2% mentioned above. It is a further object of the invention to provide a method of measurement and detectors that are particularly well suitable for disposable radiosondes, so that, by means of the method and the detectors of the invention, the detector arrangement can be made simple, of low weight and, in large-volume production, also otherwise economical.

Attempts have also been made to solve the problems discussed above by using mechanical shields as protection against min. So far, solutions with fully satisfactory operation have not been suggested for the elimination of the problems discussed above. In the commonly known modes, the problem has not been eliminated or, which is even more usual, the accuracy of humidity measurement that has been achieved is not adequate. Said shield constructions in themselves are centres of condensation and produce problems of humidity measurement.

The object of the present invention is further development of the prior art described above, in particular with respect to radiosonde applications. However, it should already be emphasized in this connection that the method in accordance with the invention can also be used elsewhere, besides in radiosondes, for example in devices for humidity measurements taking place on the ground, such as in measurements of the environment or in industry.

The object of the invention is to provide a novel method and device, wherein the problems discussed above can be substantially avoided and the drawbacks be eliminated. In view of achieving the objectives given above and those that will come out later, the method of the invention is mainly characterized in that said shield construction is heated to a temperature higher than the ambient temperature so that no substantial condensing or freezing of humidity takes place on the humidity detector or on the structures in the vicinity of same.

On the other hand, the device in accordance with the invention is mainly characterized in that said heating resistor is arranged in connection with said shield to heat the humidity detector and its environment by the intermediate of said shield and/or of a part included in same, so that the thermal energy is transferred to the environment of the humidity detector and of the shield substantially in some way other than by being conducted.

It is the inventive idea that the shield construction is heated, whereby the shield and the detector with their environment and constructions are heated, and so also the air to be measured. In such a case, the phenomenon that interferes with the measurement is eliminated, no condensation takes place on the faces which are at a temperature higher than the environment. Thus, it is essential that the heating takes place by means of a heating arrangement placed in connection with the detector shield, from which arrangement the heat is transferred, substantially in some way other than by being conducted, to the environment (to the air and the detector with its environment and support constructions). The interfering ice or humidity in general may also be placed outside the area of the detector that measures the humidity and, when it evaporates, produce a local micro-climate that distorts the measurement. It is also essential that the shield itself is heated, because interfering humidity may gather and remain on the shield.

Since the humidity detector is heated in connection with the invention and since humidity is then measured by means of the detector, the temperature of the humidity detector must be measured. When the temperature of the non-heated air and the temperature of the detector are known, the relative humidity measured by means of the detector can be corrected, for example, by means of the ratio of saturated vapour pressure, to the correct humidity. It is aim possible to include other correcting factors. The heating of the detector can be regulated in different ways. The simplest way is to connect a temperature-dependent resistor to the heating resistor so that, at the level of the tropopause ($-50°\ldots-80°$ C.), the heating is already almost completely switched off, in which case unnecessary heating that makes the measurement more difficult is omitted.

When the invention is being applied, the shape and the size of the humidity detector in themselves have no importance if they remain reasonable, but a relatively little mass and little size are favourable. The temperature of the humidity detector can be measured either by means of a temperature detector mechanically connected with the detector or by integrating the measurement of temperature as a part of the humidity detector. A third way to measure the temperature of the humidity detector is to use a little temperature detector placed at the end of long conductors as thin as possible. In such a case, the detector is placed in the air inside the shield construction. With the other ways, the transfer of heat is more sensitive to interference arising from variations in the air currents, which occur to a considerable extent, for example, in sonde operation. The measurements of temperature and humidity must have substantially the same time constants, because otherwise the errors of both of the measurements are summed in the humidity value measured and computed with different time constants. Especially in radiosonde applications, the construction of the detector must be well suitable for mass production.

Factors that should be taken into account are at least prevention of access of rain, minimized collecting of radiation heat, good flow of air to the detector, and minimized gathering of humidity and ice. The material of the detector shield itself does not have to be a good heat conductor if the thermal conductivity is, when necessary, increased by means of some other structural component of the shield, such as by means of a metal foil. The connecting of the heating construction with the detector shield may take place in highly different ways. Likewise, the heating construction can be carried into effect in a number of different ways. The heating resistor is, for example, of a resistor wire, which is connected to the detector shield in different ways as folded or wound and which is fixed, e.g., by gluing or as placed inside the shield material. The heating resistor may also consist of a, for example, vapour-deposited or glued resistor film placed on the face of the shield, and said resistor film may also be placed between the constructions in the detector shield.

The heating may take place as constant, as divided in periods in different ways, or other, vise under regulation. If necessary, the regulation of the heating may take place in a number of different ways under control, for example based on measurement of the temperature or under time control. In the simplest form, the regulation can be carried out by means of a temperature-dependent resistor that is connected in series or in parallel with the heating resistor. The function of the regulation is to heat to a suitable extent, on one hand, and to stop the heating when it is no longer needed, rather being detrimental, on the other hand.

In the following, the invention will be described in detail with reference to some environments of application and exemplifying embodiments of the invention illustrated in the figures in the accompanying drawing, the invention being not confined to the details of said environments or embodiments.

FIG. 7 is a block diagram illustration of a radiosonde measurement system in which the detector arrangement in accordance with the invention is included.

FIG. 8 illustrates a tested radiosonde system in which the detector arrangement in accordance with the invention is included.

FIGS. 9A to 9G are axonometric views or central axial sectional views of different constructional variations of the heated detector shield of the invention.

Figure 1:
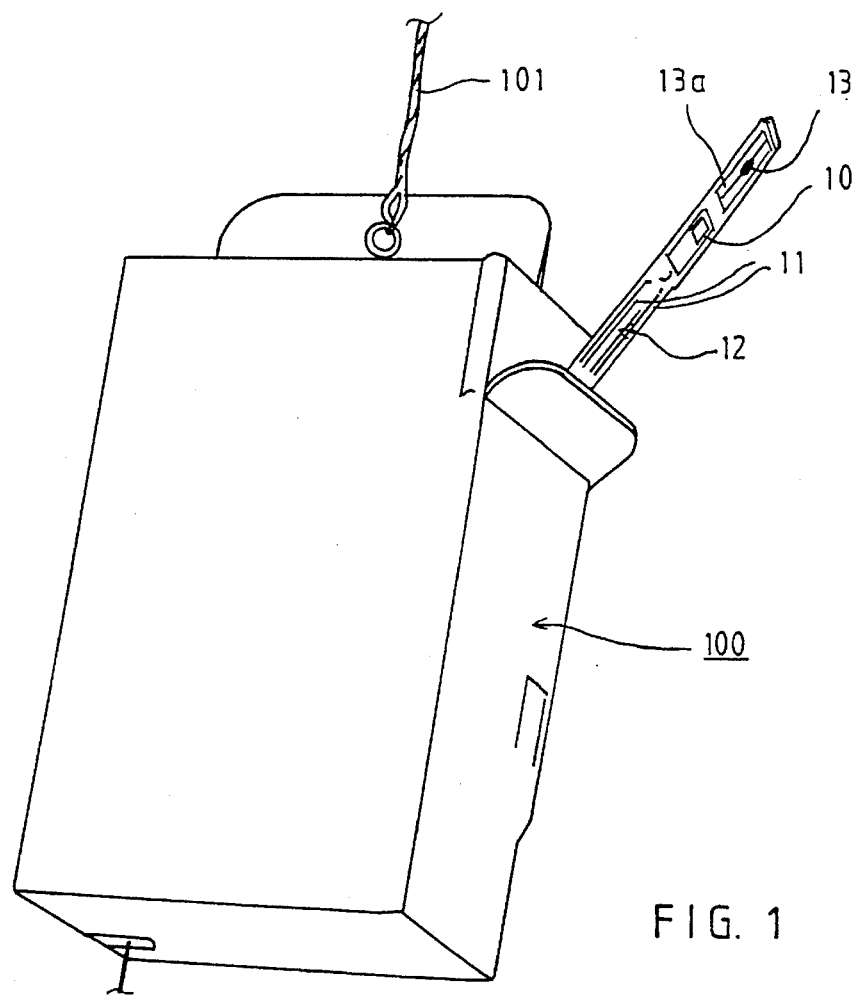
FIG. 1 is a schematic illustration of a radiosonde that operates as an environment of application of the invention.

FIG. 1 shows a radiosonde 100 as an environment of application of the invention, which radiosonde rises on support of a sonde balloon (not shown) fixed to the upper end of the wire 101. From one side of the radiosonde 100, a detector device in accordance with the invention projects, of which FIG. 1 shows the detector shield 10, the circuit card 12, the conductor patterns 11 of the detector, and the temperature detector 13 for the ambient air temperature, which detector 13 is placed in connection with the opening 13a placed at the top end of the circuit card 12.

Figure 2:
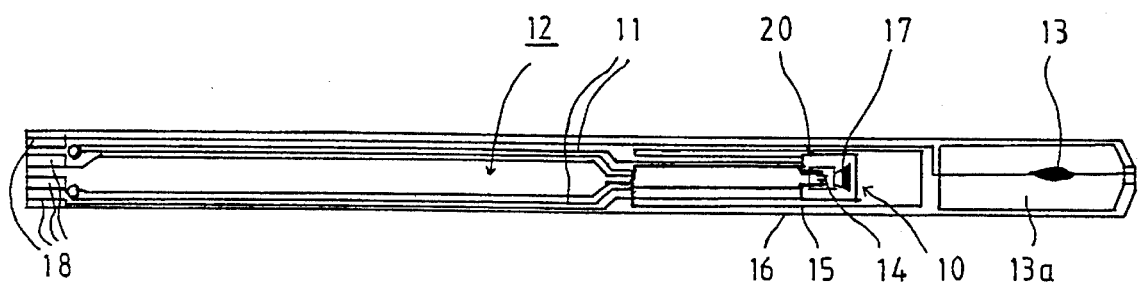
FIG. 2 is a general view of the detector arrangement in accordance with the invention and of its support construction.

FIG. 2 is a more detailed illustration of the detector arrangement with its support constructions, the humidity detector 14 and its temperature detector 17 being attached in connection with the circuit card 12 belonging to said arrangement. The detectors 14 and 17 are placed inside the cylindrical detector shield 10. From the detectors 14 and 17, the conductors 15 and 16 pass to the conductor patterns 11 on the circuit card 12, which patterns 11 transfer the measurement signals from the detectors 14 and 17 through the contacts 18 to the measurement electronics of the radiosonde 100.

Figure 3:
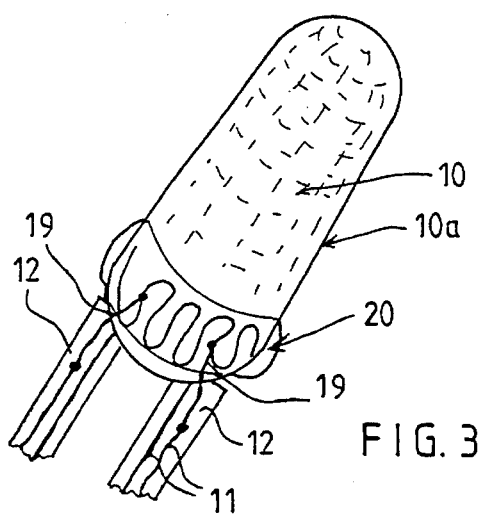
FIG. 3 is an axonometric view of a general illustration of the detector arrangement in accordance with the invention.
Figure 4:
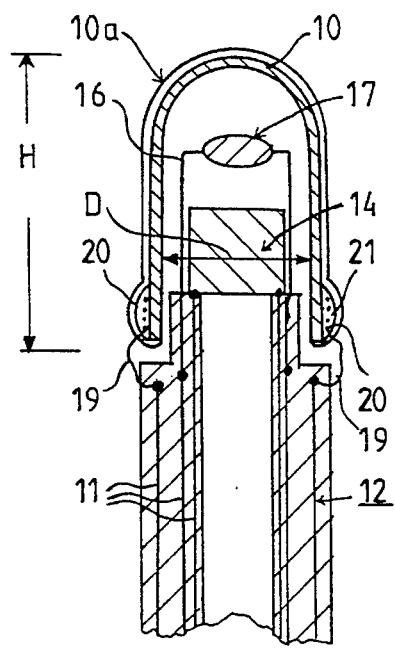
FIG. 4 is a central axial sectional view of the detector arrangement shown in FIG. 3.

FIGS. 3 and 4 are more detailed illustrations of the construction of the detector arrangement and of its detector shield 10. The shield 10 is a plastic shield with an aluminum-coated 10a outer face, in which shield, at the outer edge of the open lower end, there is a heating resistor wire 20 inside insulating adhesive 21. The metal coating on the outer face of the shield 10 increases the conduction of heat from the electrical resistor 20 and also operates as a radiation protection, which reflects solar radiation from the shield 10. According to FIG. 4, the conductors 15,16,19 pass from the detectors 14 and 17 and from the heating resistor 20 to the conductor patterns 11 on the circuit card 12. The inner diameter D of the shield 10 is typically D≈5 mm, and the height H of the shield is typically H≈10 mm. The measures of the humidity detector 14 are typically 4×4×0.4 mm. The measures of the circuit card 12 are typically 10 mm×130 mm. The other preferred measures for adjacent component parts can be concluded, e.g., from FIG. 2 in proportion to the measures given above.

Figure 5:
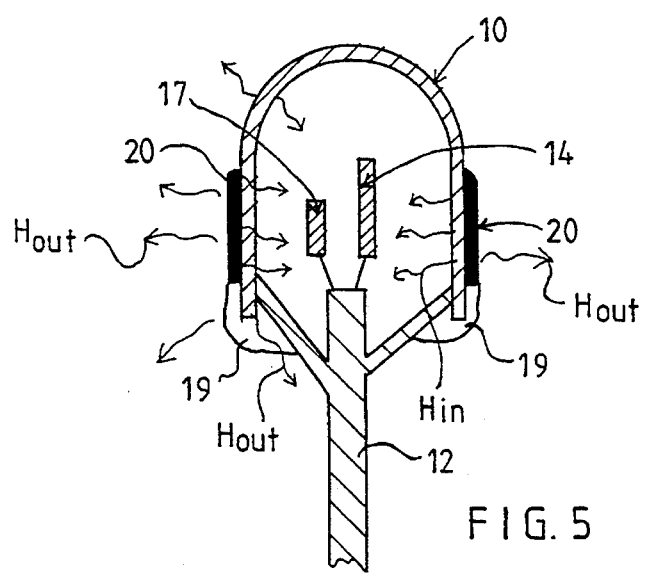
FIG. 5 is a central axial sectional view illustrating the operation of the detector arrangement in accordance with the invention.

FIG. 5 illustrates the principle of the operation of the detector arrangement in accordance with the invention. The electrical resistor 20 placed on the outer face of the shield 10 heats the shield 10, and heat radiates from it in the direction of the arrows $H_{in}$ towards the interior of the shield 10 and heats the detectors 14 and 17 and their environment. From the resistor 20 and from the shield 10, heat also radiates outside the shield 10 in the direction of the arrows $H_{out}$, which radiation heats the air in the environment outside the shield 10 and the support constructions 12 and the other constructions in the environment. It is essential that the heat is transferred from the resistor 20 and from the shield 10 into the environment substantially in some way other than by being conducted. Thus, the detectors 14 and 17, the shield 10 and the constructions in the ambient air and other constructions can be heated so that detrimental condensing and freezing of humidity do not occur on the detectors 14; 17 or on the constructions in their vicinity.

Figure 6:
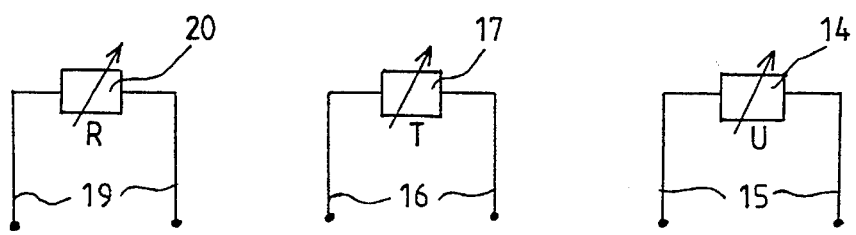
FIG. 6 shows the electrical wiring of the detector arrangement.

FIG. 6 shows the electric wiring of the detector unit in accordance with the invention, which wiring includes the heating resistor 20 of the shield 10, whose resistance R can, if necessary, be regulated in a way that will be described in more detail later. Further, the wiring includes the detector 17 for measurement of the temperature T of the humidity detector 14 and the humidity detector 14 itself, which measures the relative humidity U in its environment. The detectors 14 and 17 can be either resistive or capacitive humidity and temperature detectors.

FIG. 7 illustrates the principle of the system of measurement that makes use of the invention primarily as a block diagram. The measurement signal U of the humidity detector 14 placed inside the shield 10 is transferred along the, conductors 15 to the measurement electronics 31, to which the temperature signal $T_a$ also arrives from the detector 13 for the ambient temperature. The detector 17 for the temperature of the humidity detector 14 passes its measurement data T through the conductors 16 to the regulation and regulation-measurement electronics 30, which controls the heating current $I_H$ of the heating resistor 20 placed in connection with the shield 10. To the electronics unit 30, it is also possible to pass a separate regulation signal, such as a detector signal or a time signal, which is represented by the unit 35 illustrated with dashed lines. The power unit 32 feeds both the regulation-electronics unit 30 and the measurement-electronics unit 31. From the measurement-electronics unit 31, and so also from the regulation-electronics unit 30, the signals are passed to the correction and compensation computing unit, which, for example, compensates for the measurement signal U of the humidity detector 14 on the basis of the detector-temperature signal T of the detector. The ultimate humidity reading is displayed and/or processed further in the unit 34.

FIG. 8 illustrates a radiosonde that makes use of the detector arrangement of the invention, with its telemeter system, which system has been tested in practice with the test results that will be accounted for later. Regarding the detector system, the system is substantially similar to that described above, and the humidity detector 14 and its temperature detector 17, placed inside the shield 10, pass their measurement signals U and T to the measurement oscillator 40 of the detectors. To the measurement oscillator 40, the data on measurement of the temperature $T_a$ outside the sonde are also passed from the detector 13, and the data on measurement of the pressure P of the ambient air are passed from the detector 36. The unit 42 regulates the heating by the heating resistor 20 of the shield 10 by the intermediate of the power regulation unit 43. The active regulation element in the unit 43 is, for example, a NTC negative Temperature Coefficient resistor. The measurement oscillator 40 controls the unit 41 for transmission of the measurement data to the ground, said unit transmitting the measurement data from the sonde 100 to the ground, in a way in itself known, by means of the telemeter connection TM, the data being received on the ground by the receiver unit 44. The receiver unit 44 also receives a time signal t from an outside clock 37. The unit 44 passes the measurement data to the unit 45, where correction computing and other computing are applied to the data of humidity measurement and other measurement. The ultimate humidity reading and the other measurement data are displayed and/or processed further in the unit 46. The units 44, 45 and 46 are included in the ground systems 110 of a meteorological observation station.

FIGS. 9A to 9G are a schematic illustration of different embodiments of the heating resistor 20 fitted in connection with the detector shield 10. The outside face of the shield 10 is provided with a reflecting insulation and conductor layer 10a. This layer 10a operates as an intensifier of conduction of heat and as a reflector for outside radiation. The rest of the shield 10 is preferably made of a plastic construction.

According to FIG. 9A, in connection with the lower edge of the open side of the shield 10, a resistor wire 20A has been wound, which is fixed and insulated, e.g., inside an adhesive layer 21.

According to FIG. 9B, the heating resistor 20B consists of a resistor wire which has been bent into zigzag form, being fixed, e.g., by means of an adhesive joint.

According to FIG. 9C, to the lower edge of the shield 10, a cylindrical insulation piece 22 has been fixed, into whose groove 23 a heating resistor 20C has been wound. In the piece 22, there is a central circular opening 24 that opens into the interior of the shield 10. The piece 22 is fixed to the lower part of the opening in the shield 10, e.g., by means of adhesive or by means of a groove-projection joint.

FIG. 9D shows an embodiment in which a spiral-shaped or zigzag resistor wire has been casted into the lower edge of the plastic shield 10 so that the wires 19 of the resistor 20D extend to outside the shield 10.

FIG. 9E shows a construction in which, inside the shield 10, substantially over its entire axial length, an inner lining piece 26 similar to a coil core is fitted, into whose groove space 29 a resistor wire 20E has been wound. The central axial opening 24 in the piece 26 substantially defines the interior space in the shield 10.

FIG. 9F shows an embodiment of the invention in which, onto the outer face of the shield 10, next to the edge of its open end, a resistor film 27 has been attached as a heating resistor 20F, or a corresponding electrical resistor has been made directly by vapour-deposition on the outer face of the shield 10.

FIG. 9G shows a modification of the construction shown in FIG. 9E, in which there is a cylindrical inner lining piece 28, to whose outer face a film resistor 20G has been attached, which is fixed as placed against the inner face of the shield 10.

It is a feature common of all of the embodiments shown in FIGS. 3,4,5 and 9A . . . 9G that a dome-shaped shield is used, in which one end is closed and the other end is open, and at the open end a heating resistor 20,20A,20B,20C,20D, 20F is provided which extends across the whole circumference of the shield. FIGS. 9E and 9G show embodiments in which the heating resistors 20A and 20G extend in the axial direction of the shield 10 substantially across its entire height H.

The invention was tested in a radiosonde application as shown in FIG. 8, in which a small (diameter less than 2 mm, length about 2 mm) capacitive detector 17 placed at the ends of long wires was used for measurement of temperature, which detector 17 was placed in the air inside the shield 10 above the humidity detector 14 (measures: 4×4×0.4 mm). Measurement of the detector temperature T was successful at least with this construction, and the correction by means of computing was simple. In the tests, the heating of the shield 10 has been carried out by at its lower edge, onto the plastic shield 10, winding a resistor wire 20A (about 900 ohm). On the resistor wire 20A, there was insulating adhesive 21, and the whole shield 10 was coated normally by means of vapour-deposition with aluminum. The conductors 19 of the heating resistor 20A extended to the contact points on the circuit card 12.

From said wiring, a maximal heating power of $P_H \approx 440$ mW was obtained. In the tests, it was noticed that an adequate heating capacity was already present in the range of $P_H \approx 250 \ldots 100$ mW. In some tests, in series with the heating resistor, also a temperature-dependent NTC resistor was used, so that the heating was reduced to a great extent when the sonde waft in the stratosphere above the tropopause. FIG. 4 is an illustration of the construction of the tested detector/heating system. This detector embodiment can be accomplished in mass production, and the basic idea is independent from the constructions of the support constructions and of the shield of the detector. In the other respects, regarding its principles and its measurement technique, the radiosonde was a normal radiosonde of the applicant.

In the invention, it can be estimated that the electric power $P_H$ to be fed into the resistor 20 . . . 20 G is, as a rule, in the range of $P_H \approx 1$ mW . . . 10 W, and in sonde applications preferably $P_H \approx 1$ mW . . . 1 W. The error of measurement of the temperature T of the temperature detector 17 of the humidity detector 14 should preferably be within the limits of 0.1° . . . 0.2° C. In respect of their masses, the humidity detector 14 and the temperature detector 17 are preferably of the same order of magnitude so as to enable matched operation and peak system performance, or at least are selected have time constants of the same order.

The heating of the humidity detector 14 should not be carried out with an excessively high capacity, because of increased inaccuracies of measurement. It is preferable that, during heating, the reading of the humidity detector 14 is changed maximally by about 50%, preferably just by about 5 . . . 30%.

In the following, the patent claims will be given, and the various details of the invention may show variation within the scope of the inventive idea defined in said claims and differ from what has been stated above by way of example only.

I claim:

1. Method for measurement of relative humidity by using a humidity detector (14), in particular in radiosondes (100), in which humidity detector (14) an active material is used whose electric properties are a function of the amount of water absorbed by said material, in which method said detector (14) is heated so as to remove any ice, frost or condensed humidity gathered on its face or in its vicinity, in which method the temperature (T) of the humidity detector (14) and of the ambient temperature ($T_a$) are detected by appropriately positioned temperature detectors and these quantities are utilized along with the differences between both such temperatures as correction factors or compensation values in the computing of the humidity measurement values (U), and in which method the humidity detector (14) is protected by means of a mechanical shield construction (10) arranged around the detector, chacterized in that said shield construction (10) is heated to a temperature higher than the ambient temperature so that no substantial condensing or freezing of humidity takes place on the humidity detector (14) or on the structures in the vicinity of same.

2. Method as claimed in claim 1, characterized in that said shield construction (10) is heated electrically by means of an electrical heating resistor (20 . . . 20G) placed in connection with same so that thermal energy is transferred to the humidity detector (14) and to the peripheral environment of the detector substantially by at least one of a convective mode and a radiative mode.

3. Method as claimed in claim 2, characterized in that the intensity of the electric current ($I_H$) fed into the electrical resistor (20) placed in connection with the shield construction (10) is arranged to be adjustable in accordance with the requirement of heating said humidity detector.

4. Method as claimed in claim 3, characterized in that said regulation is carried out based on the ambient temperature ($T_a$), in radiosonde applications preferably so that, at or above the level of the tropopause ($T_a$)≈−50° . . . −80° C.), the electric current intensity responsible for the heating is substantially switched off.

5. Method as claims in claim 2, characterized in that the electric power $P_H$ of the heating of the shield construction of the detector (14) is chosen in the range of $P_H$≈1 mW . . . 10 W, in radiosonde applications preferably in the range $P_H$≈1 mW . . . 1 W.

6. Detector arrangement, in particular for radiosondes, for measurement of the relative humidity (U) of the environment, which detector arrangement comprises a humidity measurement detector (14) and a detector (17) for measurement of its temperature (T) as well as a shield (10) that surrounds said detectors (14,17), which detector arrangement includes a heating resistor (20 . . . 20G), to which electric current ($I_H$) is fed, by whose means the humidity detector (14) and its environment are heated, and which arrangement further includes a detector (13) for measurement of the ambient temperature, characterized in that said heating resistor (20 . . . 20G) is operatively associated with said shield (10) to heat the shield relative to the humidity detector (14) and its environment, so that the heated shield functions as an intermediary operative to transfer thermal energy to the environment of the humidity detector (14) and of the shield (10) substantially by at least one of a convective mode and a radiative mode.

7. Detector arrangement as claimed in claim 6, wherein the shield consists of a cup-shaped shield (10) that is at least partly open at one end and in whose interior said humidity detector (14) and its temperature detector (17) are placed, characterized in that, in connection with said shield (10), at least on the portion of its open side, an electrical resistor (20;20A;20B;20C;20D;20F) is fitted into the shield, and into which resistor heating current ($I_H$) can be fed.

8. Detector arrangement as claimed in claim 6, characterized in that said electrical resistor consists of a resistor wire (20A) wound at the edge of the open side of the shield (10), of a resistor wire (20B) bent into zigzag shape, of a resistor wire (20D) inlaid in the insulating material of the shield, and/or of a resistor film (20F) directly vapour-deposited or glued onto the outer face of the shield.

9. Detector arrangement as claimed in claim 6, characterized in that into the interior of the shield (10), an insulation piece (22; 26) has been fixed, into whose groove space or equivalent a resistor wire (20C; 20D) has been wound.

10. Detector arrangement as claimed in claim 6, characterized in that, in the interior of the shield (10), an inner lining piece (26; 28) extending substantially across its axial length (H) is fitted, around which lining piece, against the inner face of the shield (10), a heating resistor for heating the shield (10) and consisting of a resistor wire (20E) and/or of a film resistor (20G) is fitted (FIGS. 9E and 9G).

11. Detector arrangement as claimed in claim 6, characterized in that the detector arrangement includes a measurement-electronics unit (31), to which the humidity detector (14) and the detector (13) for measurement of the outside temperature ($T_a$) are connected, that the detector arrangement includes a regulation and/or regulation-measurement electronics unit (30), to which the detector (17) for measurement of the temperature (T) of the humidity detector (14) is connected and which unit (30) is arranged to regulate the electric current ($I_H$) fed into the shield (20), and that said units (30, 31) are connected to the correction and compensation computing unit (33), from which a temperature-compensated humidity reading can be obtained (FIG. 7).

\* \* \* \* \*